US011028159B2

(12) United States Patent
Dempsey et al.

(10) Patent No.: US 11,028,159 B2
(45) Date of Patent: Jun. 8, 2021

(54) COMPOSITION AND METHODS FOR TREATING SNAKE ENVENOMATION

(71) Applicant: VENOMYX, INC., San Diego, CA (US)

(72) Inventors: Daniel Thomas Dempsey, San Diego, CA (US); Deepankar Roy, San Diego, CA (US); Alexio Capovilla, Carlsbad, CA (US)

(73) Assignee: VENOMYX, INC., San Diego, CA (US)

( * ) Notice: Subject to any disclaimer, the term of this patent is extended or adjusted under 35 U.S.C. 154(b) by 0 days.

(21) Appl. No.: 16/610,836

(22) PCT Filed: Apr. 26, 2018

(86) PCT No.: PCT/US2018/029498
§ 371 (c)(1),
(2) Date: Nov. 4, 2019

(87) PCT Pub. No.: WO2018/204153
PCT Pub. Date: Nov. 8, 2018

(65) Prior Publication Data
US 2020/0157197 A1 May 21, 2020

Related U.S. Application Data

(60) Provisional application No. 62/500,372, filed on May 2, 2017.

(51) Int. Cl.
*C07K 16/18* (2006.01)
(52) U.S. Cl.
CPC ........ *C07K 16/18* (2013.01); *C07K 2317/565* (2013.01); *C07K 2317/567* (2013.01)
(58) Field of Classification Search
None
See application file for complete search history.

(56) References Cited

U.S. PATENT DOCUMENTS

| | | |
|---|---|---|
| 2009/0104218 A1 | 4/2009 | Tettelin et al. |
| 2009/0291085 A1 | 11/2009 | Schoeberl et al. |
| 2013/0059752 A1 | 3/2013 | Bodary-Winter et al. |

OTHER PUBLICATIONS

Gahroudi, Frontiers in Immunology, 8:Article 159, pp. 1-8, 2017.*
UniProt Database Accession No. AOAOG2C8A5 published Sep. 16, 2015.*
WO, International Search Report and Written Opinion, Application No. PCT/US18/29498, dated Oct. 1, 2018.
Kashima, Simone, et al., "Analysis of Bothrops jararacussu venomous gland transcriptome focusing on structural and functional aspects1: I-gene expression profile of highly expressed pohspholipasesA2," Biochemie, vol. 86, pp. 211-219 (Mar. 9, 2004).
Nunez, Vitelbina, et al., "Structural and functional characterization of myotoxin I, a Lys49 phospholipase A2 homologue from the venom of a snake Bothrops atrox," Toxicon, vol. 44, No. 1 pp. 91-101 (Jul. 2004).
Prado, Nidiane, et al., "Inhibition of the Myotoxicity Induced by Bothrops jararacussu Venom and Isolated Phospholipase A2 by Specific Camelid Single-Doman Antibody Fragments," PLOS ONE, vol. 11, No. 3, e0151363, pp. 1-22 (Mar. 30, 2016).
Beckman, RA, et al., Antibody constructs in cancer therapy: protein engineering strategies to improve exposure in solid tumors, Cancer, 109:170-179 (2007).
Bourne, Y., et al., Crystal structure of α-Cbtx-AChBP complex reveals essential interactions between snake α-neurotoxins and nicotinic receptors, EMBO J., 24:1512-1522 (2005).
Bruce, Virginia J., et al., "Resurfaced cell-penetrating nanobodies: A potentially general scaffold for intracellularly targeted protein discovery," Protein Sci., 25:1129-1137 (2016).
Bulbring, E., "Observation on the isolated phrenic nerve-diaphragm preparation of the rat," Brit. J. Pharmacol, 1:38-61 (1946).
Calvete, Juan J.; et al., "Venoms, venomics, antivenomics," FEBS Lett., 583:1736-1743 (2009).
Cheng, Yun-Ching, et al., "B chain is a functional subunit of beta-bungarotoxin for inducing apoptotic death of human neuroblastoma SK—N—SH cells," Toxicon, 51 (2):304-315 (2008).
Chippaux, J. P., "Snake-bites: appraisal of the global situation," Bulletin of WHO, 76(5):515-524 (1998).
Chotwiwatthanakun, Charoonroj, et al., "Production of potent polyvalent antivenom against three elapid venoms using a low dose, low volume, multi-site immunization protocol," Toxicon, 39:1487-1494 (2001).
Cortez-Retamozo, Virna, et al., "Efficient Tumor Targeting by Single-Domain Antibody Fragments of Camels," Int. J. Cancer, 98:456-462 (2002).
Cortez-Retamozo, Virna, et al., "Efficient Cancer Therapy with a Nanobody-Based Conjugate," Cancer Res., 64:2853-2857 (2004).
Frenken, Leon G.J., et al., "Isolation of antigen specific Llama VHH antibody fragment and their high level of secretion by Saccharomyces cerevisiae," J. Biotech., 78:11-21 (2000).
Ghahroudi, M. Arbabi, et al., "Selection and identification of single domain antibody fragments from camel heavy-chain antibodies," FEBS Lett., 414:521-526 (1997).
Gutierrez, Jose Maria, et al., "Neutralization of local tissue damage induced by Bothrops asper (terciopelo) snake venom," Toxicon, 36(11):1529-1536 (1998).
Gutierrez, Jose Maria, et al., "Snake venom metalloproteinases: Their role in pathogenesis of local tissue damage," Biochimie, 82:841-850 (2000).
Gutierrez, Jose Maria, et al., Confronting the neglected Problem of Snake Bite Envenoming: The Need for a Global Partnership, PLoS Med, 3(6):e150. (2006).

(Continued)

*Primary Examiner* — Patricia Duffy
(74) *Attorney, Agent, or Firm* — Orrick, Herrington & Sutcliffe LLP

(57) ABSTRACT

The invention generally relates to compositions and methods for treating snake envenomation in animals, including humans. In some aspects, the invention provides therapeutic compositions that contain one or more toxin binding molecules including, for example, anti-toxin antibodies and binding fragments.

16 Claims, 5 Drawing Sheets

Specification includes a Sequence Listing.

(56) References Cited

OTHER PUBLICATIONS

Hamers-Casterman, C., et al., "Naturally occurring antibodies devoid of light chains," Nature, 363:446-448 (Jun. 1993).
Harmsen, Michiel M., et al. "Llama heavy-chain V regions consist of at least four distinct subfamilies revealing novel sequence features," Mol Immunol, 37:579-590 (2000).
Harrison, Robert A., et al., "Snake envenoming: a disease of poverty," PLoS Negl Trop Dis. 3(12):e569 (2009).
Hsu, Hung-Ju, et al., "Antibody Variable Domain Interface and Framework Sequence Requirements for Stability and Function by High-Throughput Experiments," Structure, 22:22-34 (Jan. 7, 2014).
Inoue, Seiji, et al. "Amino acid sequence of a cytotoxin-like basic protein with low cytotoxic activity from the venom of the Thailand cobra *Naja siamensis*," FEB 04799, 218(1):17-21 (Jun. 1987).
Kabat E.A., et al., "Identical V region amino acid sequences and segments of sequences in antibodies of different specificities. Relative contributions of VH and VL genes, minigenes, and complementarity-determining regions to binding of antibody-combining sites," J Immunol, 147:1709-1719 (1991).
Lalloo, David G., et al., "Snake antivenoms," J. Toxicol. Clin. Toxicol., 41(3):277-290 (2003).
Minton, S. A., "Neurotoxic snake envenoming," Semin. Neurol., 10(1): 52-61 (Mar. 1990).
Moura-Da-Silva, A.M.; et al., "Importance of snake venom metalloproteinases in cell biology: Effects on platelets, inflammatory and endothelial cells," Curr. Pharm. Des., 13:2893-2905 (2007).
Moura-Da-Silva, Ana M., et al., "Processing of Snake Venom Metalloproteinases: Generation of Toxin Diversity and Enzyme Inactivation," Toxins, 8:183, 15 pages (2016).

Moutel, Sandrine, et al., "NaLi—H1: A universal synthetic library of humanized nanobodies providing highly functional antibodies and intrabodies," eLife 5:e16228 (2016).
Muruganandam, A., et al., Selection of phage-displayed llama single-domain antibodies that transmigrate across human blood-brain barrier endothelium, FASEB J. 16: 240-242 (2002).
Pratanaphon, Ronachai, et al., Production of highly potent horse antivenom against the Thai cobra (*Naja kaouthia*), Vaccine 15(14):1523-1528 (1997).
Serrano, Solange M.T., The long road of research on snake venom serine proteinases, Toxicon 62:19-26 (2013).
Sousa, L.F., et al., "Comparison of phylogeny, venom composition and neutralization by antivenom in diverse species of bothrops complex," PLoS Negl. Trop. Dis. 7(9):e2442 (2013).
Stewart, Christine S., et al., Isolation, characterization and pentamerization of α-cobrotoxin specific single-domain antibodies from a naïve phage display library: Preliminary findings for antivenom development, Toxicon, 49: 699-709 (2007).
Vincke, Cecile, et al., "General Strategy to Humanize a Camelid Single-domain Antibody and Identification of a Universal Humanized Nanobody Scaffold," J. Bio. Chem., 284(5): 3273-3284 (Jan. 20, 2009).
Viravan, Chaisin., et al., ELISA confirmation of acute and past envenoming by the monocellate Thai cobra (*Naja kaouthia*), Am. J. Trop. Med. Hyg., 35(1):173-181 (1986).
Vu, K. B., et al., Comparison of llama VH sequences from conventional and heavy chain antibodies. Mol. Immunol., 34(16-17): 1121-1131 (1997).
Who, Rabies and envenomings. A neglected public health issue. Geneva: World Health Organization (2007).
Yang, C.C., "Structure and function of Cobrotoxin," Journal of Toxicology: Toxin Reviews, 13(3):275-290 (1994).

* cited by examiner

|  | C. atrox | C. rhod | B. cand | N. siam | N. sput | O. hann | D. acut | B. caer | N. kaou (I) |
|---|---|---|---|---|---|---|---|---|---|
| α-PLA2 | 1.1562 | 0.017 | 0.0105 | 0.0042 | 0.0038 | 0.1353 | 0.8823 | 0.0114 | 0.0018 |
| α-bungarotoxin | 0.1571 | 0.0793 | 0.0733 | 0.0366 | 0.0772 | 0.3555 | 0.7973 | 0.1737 | 0.1009 |
| α-cobrotoxin | 0 | 0 | 0.0207 | 0.051 | 0.0698 | 0.766 | 0.0889 | 0.1679 | 0 |
| α-SVMP (B6) | 0.0194 | 0.1492 | 0.0119 | 0.1266 | 0.1479 | 0.4984 | 0.1256 | 0.0186 | 0.1822 |
| α-SVMP (D11) | 0.0911 | 0.1065 | 0 | 0 | 0 | 0.0816 | 0.0342 | 0 | 0 |

|  | N. kaou (T) | E. carin | C. adma | C. hell | C. scut (A) | C. scut (B) | A. leuc | A pisc. | D. russ |
|---|---|---|---|---|---|---|---|---|---|
| α-PLA2 | 0.0044 | 1.9736 | 0.6704 | 0.3657 | 0.0036 | 0.6931 | 2.9454 | 2.8108 | 2.852 |
| α-bungarotoxin | 0.0826 | 1.1679 | x | x | x | x | x | x | x |
| α-cobrotoxin | 0 | 0 | x | x | x | x | x | x | x |
| α-SVMP (B6) | 0.1492 | 0.0444 | x | x | x | x | x | x | x |
| α-SVMP (D11) | 0 | 0 | x | x | x | x | x | x | x |

Fig. 5

```
                         SEQUENCE LISTING

<160> NUMBER OF SEQ ID NOS: 42

<210> SEQ ID NO 1
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Ala Gln Val Gln Leu Gln Glu Ser Gly Gly Gly Leu Val Ala Pro
1               5                   10                  15

Gly Gly Ser Leu Arg Leu Ser Cys Ala Ala Ser Glu Asn Ile Arg Val
            20                  25                  30

Lys Ala Met Gly Trp Tyr Arg Gln Thr Pro Gly Lys Gln Arg Glu Leu
        35                  40                  45

Val Ala Thr Ile Ser Ala Arg Pro Ser Gly Gly Ile Thr Asn Tyr Val
    50                  55                  60

Asp Pro Val Lys Gly Arg Phe Thr Ile Ser Arg Asp Asn Ala Lys Asn
65                  70                  75                  80

Val Leu Tyr Leu Gln Met Asn Ser Leu Lys Pro Glu Asp Thr Gly Val
                85                  90                  95

Tyr Tyr Cys Asn Ile Val Gly Thr Asn Ile Trp Gly Gln Gly Thr Gln
            100                 105                 110

Val Thr Val Ser Ser Thr Ser Gly Pro Gly Gly Gln His His His His
        115                 120                 125

His His Gly Ala Glu Gln Lys Leu Ile Ser Glu Glu Asp Leu Ser
    130                 135                 140

<210> SEQ ID NO 2
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Ala Gln Val Gln Leu Gln Glu Ser Gly Gly Gly Leu Val Gln Ala
1               5                   10                  15

Gly Gly Ser Leu Arg Leu Ser Cys Ala Ala Ser Gly Arg Thr Phe Ser
            20                  25                  30

Ser Ala Ala Met Gly Trp Phe Arg Arg Ala Pro Gly Glu Glu Arg Glu
        35                  40                  45
```

```
Phe Val Ala Ala Ile Ser Trp Ser Gly Gly Thr Thr His Tyr Thr Glu
 50                  55                  60

Ser Val Lys Gly Arg Phe Thr Ile Ser Arg Asp Asn Ala Lys Asn Thr
 65                  70                  75                  80

Val Ser Leu Gln Met Asp Ser Leu Lys Pro Glu Asp Thr Ala Ile Tyr
             85                  90                  95

Tyr Cys Ala Ala Asp Met Ala Leu Ser Thr Val Val Glu Gly Thr Ser
            100                 105                 110

Arg Tyr Trp Gly Gln Gly Thr Gln Val Thr Val Ser Ser Thr Ser Gly
            115                 120                 125

Pro Gly Gly Gln His His His His His Gly Ala Glu Gln Lys Leu
            130                 135                 140

Ile Ser Glu Glu Asp Leu Ser
145                 150

<210> SEQ ID NO 3
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Ala Gln Val Gln Leu Gln Glu Ser Gly Gly Gly Leu Val Gln Ala
 1               5                  10                  15

Gly Asp Ser Leu Arg Leu Ser Cys Ala Ala Ser Gly His Thr Phe Arg
             20                  25                  30

Asp Arg Ala Met Asn Trp Phe Arg Gln Ala Pro Gly Lys Glu Arg Glu
             35                  40                  45

Phe Val Ala Ala Ile His Trp Ser Asp Gly Arg Thr Phe Tyr Thr Asp
 50                  55                  60

Ser Val Lys Gly Arg Phe Thr Ile Ser Arg Asp Asn Ala Lys Asn Thr
 65                  70                  75                  80

Gly Tyr Leu Gln Met Asn Ser Leu Lys Thr Glu Asp Thr Ala Val Tyr
             85                  90                  95

Tyr Cys Ala Ile Val Met Ala Tyr Pro Trp Thr Thr Pro Gly Gly Ile
            100                 105                 110

Asn Asp Trp Gly Lys Gly Thr Leu Val Thr Val Ser Ser Thr Ser Gly
            115                 120                 125

Pro Gly Gly Gln His His His His His Gly Ala Glu Gln Lys Leu
            130                 135                 140

Ile Ser Glu Glu Asp Leu Ser
145                 150

<210> SEQ ID NO 4
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Ala Gln Val Gln Leu Gln Glu Ser Gly Gly Gly Leu Ala Gln Ala
 1               5                  10                  15

Gly Gly Ser Leu Arg Leu Ser Cys Ser Ala Ser Arg Asn Ile Phe Arg
             20                  25                  30
```

```
Val Tyr Gly Trp Tyr Arg Gln Ala Pro Gly Lys Gln Arg Glu Trp Val
         35                  40                  45

Ala Ser Ile Thr Arg Asp Asp Ser Thr Ala Tyr Ala Asp Ser Val Lys
     50                  55                  60

Gly Arg Phe Thr Ile Ser Arg Asp Ser Ala Lys Asn Thr Met Tyr Leu
 65              70                  75                  80

Gln Met Ser Ser Leu Arg Leu Glu Asp Thr Thr Tyr Tyr Cys Ala
                 85                  90                  95

Ala Gln Ser Ile Ser Gly Thr Ile Gln Trp Gly Gln Gly Thr Gln Val
            100                 105                 110

Thr Val Ser Ser Thr Ser Gly Pro Gly Gly Gln His His His His
             115                 120                 125

His Gly Ala Glu Gln Lys Leu Ile Ser Glu Glu Asp Leu Ser
130                 135                 140
```

<210> SEQ ID NO 5
<211> LENGTH: 151
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

```
Leu Ala Gln Val Gln Leu Gln Gln Ser Gly Gly Gly Leu Val Gln Ala
 1               5                  10                  15

Gly Asp Ser Leu Arg Leu Ser Cys Ala Ala Ser Gly Arg Thr Phe Arg
             20                  25                  30

Asp Arg Ala Met Asn Trp Phe Arg Gln Ala Pro Gly Lys Glu Arg Glu
         35                  40                  45

Phe Val Ala Ala Ile His Trp Ser Asp Gly Arg Thr Tyr Tyr Ala Asp
     50                  55                  60

Ser Val Lys Gly Arg Phe Thr Ile Ser Arg Asp Asn Ala Lys Asn Thr
 65              70                  75                  80

Gly Ser Leu Gln Met Asp Ser Leu Lys Thr Glu Asp Thr Gly Val Tyr
             85                  90                  95

Tyr Cys Ala Ile Val Met Ala Tyr Pro Trp Thr Thr Pro Gly Gly Ile
            100                 105                 110

Asn Asp Trp Gly Lys Gly Thr Leu Val Thr Val Ser Ser Thr Ser Gly
            115                 120                 125

Pro Gly Gly Gln His His His His His Gly Ala Glu Gln Lys Leu
            130                 135                 140

Ile Ser Glu Glu Asp Leu Ser
145                 150
```

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

```
Glu Asn Ile Arg Val Lys Ala
 1               5
```

```
<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Arg Thr Phe Ser Ser Ala Ala
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly His Thr Phe Arg Asp Arg Ala
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Asn Ile Phe Arg Val
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Arg Thr Phe Arg Asp Arg Ala
1               5

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ile Ser Ala Arg Pro Ser Gly Gly Ile Thr
1               5                   10

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 12

Ile Ser Trp Ser Gly Gly Thr Thr
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ile His Trp Ser Asp Gly Arg Thr
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ile Thr Arg Asp Asp Ser Thr
1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ile His Trp Ser Asp Gly Arg Thr
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asn Ile Val Gly Thr Asn Ile
1               5

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Ala Asp Met Ala Leu Ser Thr Val Val Glu Gly Thr Ser Arg Tyr
1               5                   10                  15
```

```
<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Ile Val Met Ala Tyr Pro Trp Thr Thr Pro Gly Gly Ile Asn Asp
1               5                   10                  15

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Ala Gln Ser Ile Ser Gly Thr Ile Gln
1               5                   10

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Ile Val Met Ala Tyr Pro Trp Thr Thr Pro Gly Gly Ile Asn Asp
1               5                   10                  15

<210> SEQ ID NO 21
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Met Ala Gln Val Gln Leu Gln Glu Ser Gly Gly Gly Leu Val Ala Pro
1               5                   10                  15

Gly Gly Ser Leu Arg Leu Ser Cys Ala Ala Ser
            20                  25

<210> SEQ ID NO 22
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Met Ala Gln Val Gln Leu Gln Glu Ser Gly Gly Gly Leu Val Gln Ala
1               5                   10                  15

Gly Gly Ser Leu Arg Leu Ser Cys Ala Ala Ser
            20                  25
```

```
<210> SEQ ID NO 23
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Met Ala Gln Val Gln Leu Gln Glu Ser Gly Gly Gly Leu Val Gln Ala
1               5                   10                  15

Gly Asp Ser Leu Arg Leu Ser Cys Ala Ala Ser
            20                  25

<210> SEQ ID NO 24
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Met Ala Gln Val Gln Leu Gln Glu Ser Gly Gly Gly Leu Ala Gln Ala
1               5                   10                  15

Gly Gly Ser Leu Arg Leu Ser Cys Ser Ala Ser
            20                  25

<210> SEQ ID NO 25
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Leu Ala Gln Val Gln Leu Gln Gln Ser Gly Gly Gly Leu Val Gln Ala
1               5                   10                  15

Gly Asp Ser Leu Arg Leu Ser Cys Ala Ala Ser
            20                  25

<210> SEQ ID NO 26
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Met or Leu
<220> FEATURE:
<221> NAME/KEY: MOD_RES
<222> LOCATION: (8)..(8)
<223> OTHER INFORMATION: Gln or Glu
<220> FEATURE:
<221> NAME/KEY: MOD_RES
<222> LOCATION: (14)..(14)
<223> OTHER INFORMATION: Val or Ala
<220> FEATURE:
<221> NAME/KEY: MOD_RES
<222> LOCATION: (15)..(15)
<223> OTHER INFORMATION: Gln or Ala
<220> FEATURE:
<221> NAME/KEY: MOD_RES
<222> LOCATION: (17)..(17)
<223> OTHER INFORMATION: Gly or Asp
```

<220> FEATURE:
<221> NAME/KEY: MOD_RES
<222> LOCATION: (24)..(24)
<223> OTHER INFORMATION: Ser or Ala

<400> SEQUENCE: 26

Xaa Ala Gln Val Gln Leu Gln Xaa Ser Gly Gly Gly Leu Xaa Xaa Gly
1               5                   10                  15

Xaa Ser Leu Arg Leu Ser Cys Xaa Ala Ser
            20                  25

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Met Gly Trp Tyr Arg Gln Thr Pro Gly Lys Gln Arg Glu Leu Val Ala
1               5                   10                  15

Thr

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Met Gly Trp Phe Arg Arg Ala Pro Gly Glu Glu Arg Glu Phe Val Ala
1               5                   10                  15

Ala

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Met Asn Trp Phe Arg Gln Ala Pro Gly Lys Glu Arg Glu Phe Val Ala
1               5                   10                  15

Ala

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Tyr Gly Trp Tyr Arg Gln Ala Pro Gly Lys Gln Arg Glu Trp Val Ala
1               5                   10                  15

Ser

```
<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Met Asn Trp Phe Arg Gln Ala Pro Gly Lys Glu Arg Glu Phe Val Ala
1               5                   10                  15

Ala

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Met or Tyr
<220> FEATURE:
<221> NAME/KEY: MOD_RES
<222> LOCATION: (2)..(2)
<223> OTHER INFORMATION: Gly or Asn
<220> FEATURE:
<221> NAME/KEY: MOD_RES
<222> LOCATION: (4)..(4)
<223> OTHER INFORMATION: Phe or Tyr
<220> FEATURE:
<221> NAME/KEY: MOD_RES
<222> LOCATION: (6)..(6)
<223> OTHER INFORMATION: Arg or Gln
<220> FEATURE:
<221> NAME/KEY: MOD_RES
<222> LOCATION: (7)..(7)
<223> OTHER INFORMATION: Ala or Thr
<220> FEATURE:
<221> NAME/KEY: MOD_RES
<222> LOCATION: (10)..(10)
<223> OTHER INFORMATION: Lys or Glu
<220> FEATURE:
<221> NAME/KEY: MOD_RES
<222> LOCATION: (11)..(11)
<223> OTHER INFORMATION: Gln or Glu
<220> FEATURE:
<221> NAME/KEY: MOD_RES
<222> LOCATION: (14)..(14)
<223> OTHER INFORMATION: Phe, Leu, or Trp
<220> FEATURE:
<221> NAME/KEY: MOD_RES
<222> LOCATION: (17)..(17)
<223> OTHER INFORMATION: Ala, Ser, or Thr

<400> SEQUENCE: 32

Xaa Xaa Trp Xaa Arg Xaa Xaa Pro Gly Xaa Xaa Arg Glu Xaa Val Ala
1               5                   10                  15

Xaa

<210> SEQ ID NO 33
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 33

Asn Tyr Val Asp Pro Val Lys Gly Arg Phe Thr Ile Ser Arg Asp Asn
1               5                   10                  15

Ala Lys Asn Val Leu Tyr Leu Gln Met Asn Ser Leu Lys Pro Glu Asp
            20                  25                  30

Thr Gly Val Tyr Tyr Cys
        35

<210> SEQ ID NO 34
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

His Tyr Thr Glu Ser Val Lys Gly Arg Phe Thr Ile Ser Arg Asp Asn
1               5                   10                  15

Ala Lys Asn Thr Val Ser Leu Gln Met Asp Ser Leu Lys Pro Glu Asp
            20                  25                  30

Thr Ala Ile Tyr Tyr Cys
        35

<210> SEQ ID NO 35
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Phe Tyr Thr Asp Ser Val Lys Gly Arg Phe Thr Ile Ser Arg Asp Asn
1               5                   10                  15

Ala Lys Asn Thr Gly Tyr Leu Gln Met Asn Ser Leu Lys Thr Glu Asp
            20                  25                  30

Thr Ala Val Tyr Tyr Cys
        35

<210> SEQ ID NO 36
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Ala Tyr Ala Asp Ser Val Lys Gly Arg Phe Thr Ile Ser Arg Asp Ser
1               5                   10                  15

Ala Lys Asn Thr Met Tyr Leu Gln Met Ser Ser Leu Arg Leu Glu Asp
            20                  25                  30

Thr Ser Thr Tyr Tyr Cys
        35

<210> SEQ ID NO 37
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 37

Tyr Tyr Ala Asp Ser Val Lys Gly Arg Phe Thr Ile Ser Arg Asp Asn
1               5                   10                  15

Ala Lys Asn Thr Gly Ser Leu Gln Met Asp Ser Leu Lys Thr Glu Asp
            20                  25                  30

Thr Gly Val Tyr Tyr Cys
        35

<210> SEQ ID NO 38
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ala, Phe, His, Asn, or Tyr
<220> FEATURE:
<221> NAME/KEY: MOD_RES
<222> LOCATION: (3)..(3)
<223> OTHER INFORMATION: Ala, Thr, or Val
<220> FEATURE:
<221> NAME/KEY: MOD_RES
<222> LOCATION: (4)..(4)
<223> OTHER INFORMATION: Asp or Glu
<220> FEATURE:
<221> NAME/KEY: MOD_RES
<222> LOCATION: (5)..(5)
<223> OTHER INFORMATION: Ser or Pro
<220> FEATURE:
<221> NAME/KEY: MOD_RES
<222> LOCATION: (16)..(16)
<223> OTHER INFORMATION: Asn or Ser
<220> FEATURE:
<221> NAME/KEY: MOD_RES
<222> LOCATION: (20)..(20)
<223> OTHER INFORMATION: Thr or Val
<220> FEATURE:
<221> NAME/KEY: MOD_RES
<222> LOCATION: (21)..(21)
<223> OTHER INFORMATION: Gly, Leu, Met, or Val
<220> FEATURE:
<221> NAME/KEY: MOD_RES
<222> LOCATION: (22)..(22)
<223> OTHER INFORMATION: Ser or Tyr
<220> FEATURE:
<221> NAME/KEY: MOD_RES
<222> LOCATION: (26)..(26)
<223> OTHER INFORMATION: Asp, Asn, or Ser
<220> FEATURE:
<221> NAME/KEY: MOD_RES
<222> LOCATION: (29)..(29)
<223> OTHER INFORMATION: Lys or Arg
<220> FEATURE:
<221> NAME/KEY: MOD_RES
<222> LOCATION: (30)..(30)
<223> OTHER INFORMATION: Leu, Pro, or Thr
<220> FEATURE:
<221> NAME/KEY: MOD_RES
<222> LOCATION: (34)..(34)
<223> OTHER INFORMATION: Ala, Gly, or Ser
<220> FEATURE:
<221> NAME/KEY: MOD_RES
<222> LOCATION: (35)..(35)
<223> OTHER INFORMATION: Ile, Thr, or Val

```
<400> SEQUENCE: 38

Xaa Tyr Xaa Xaa Xaa Val Lys Gly Arg Phe Thr Ile Ser Arg Asp Xaa
1               5                   10                  15

Ala Lys Asn Xaa Xaa Xaa Leu Gln Met Xaa Ser Leu Xaa Xaa Glu Asp
            20                  25                  30

Thr Xaa Xaa Tyr Tyr Cys
        35

<210> SEQ ID NO 39
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Trp Gly Gln Gly Thr Gln Val Thr Val Ser Ser Thr Ser Gly Pro Gly
1               5                   10                  15

Gly Gln His His His His His His Gly Ala Glu Gln Lys Leu Ile Ser
            20                  25                  30

Glu Glu Asp Leu Ser
        35

<210> SEQ ID NO 40
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Trp Gly Lys Gly Thr Leu Val Thr Val Ser Ser Thr Ser Gly Pro Gly
1               5                   10                  15

Gly Gln His His His His His His Gly Ala Glu Gln Lys Leu Ile Ser
            20                  25                  30

Glu Glu Asp Leu Ser
        35

<210> SEQ ID NO 41
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Lys or Gln
<220> FEATURE:
<221> NAME/KEY: MOD_RES
<222> LOCATION: (6)..(6)
<223> OTHER INFORMATION: Leu or Gln

<400> SEQUENCE: 41

Trp Gly Xaa Gly Thr Xaa Val Thr Val Ser Ser Thr Ser Gly Pro Gly
1               5                   10                  15

Gly Gln His His His His His His Gly Ala Glu Gln Lys Leu Ile Ser
            20                  25                  30

Glu Glu Asp Leu Ser
        35
```

```
<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
atgaaatacc tattgcctac gg                                          22
```

COMPOSITION AND METHODS FOR TREATING SNAKE ENVENOMATION

CROSS-REFERENCE TO RELATED APPLICATIONS

This application is a national phase application from International Application No. PCT/US2018/029498, filed on Apr. 26, 2018, which claims priority of U.S. Provisional Application No. 62/500,372, filed May 2, 2017 Priority to the preceding patent applications is expressly claimed, and the disclosures of the preceding applications are hereby incorporated herein by reference in their entireties and for all purposes.

FIELD

The invention generally relates to compositions and methods for treating snake envenomation in humans and animals. In some aspects, the invention provides therapeutic compositions that contain one or more toxin binding molecules including, for example, anti-toxin antibodies and binding fragments.

BACKGROUND OF THE INVENTION

Envenomings due to snake bite are one of the largest and most neglected tropical diseases with a profound effect on people living in the topical or subtropical regions of Africa, Asia, Latin America, and Oceania (Gutierrez 2006; Harrison 2009; WHO 2007). Over 5 million estimated snake bite cases occur worldwide each year, greater than half of which cause envenomation, causing around 125,000 human deaths and (Chippaux 2006) and hundreds of thousands more cases of permanent disability. Snake venoms are complex mixtures of several proteins and peptides, several of which are toxins that cause damage due to snakebites. Among the major toxin components are metalloproteinases, phospholipase A2, serine proteases, neurotoxins, and many others that cause clinical manifestation of snakebite.

Envenomation by venomous snakes, depending on the species of snake is usually manifested by neurotoxicity, extensive local tissue necrosis (Viravan et al. 1986), cytotoxicity, and hemotoxicity. We have initially chosen five toxins in snake venoms to target and neutralize with camelid sdAb-$V_H$H fragments: snake venom metalloproteinase (SVMP), snake venom phospholipase A2 (svPLA2), snake venom serine protease (SVSP), cobrotoxin and beta-bungarotoxin.

Snake venom metalloproteinases (SVMPs) (Moura-da-Silva et al. 2016) are one of the most abundant components on snake venoms, especially in most species of viperidae family (Sousa et al. 2013; Calvete et al. 2009). SVMPs can cause hemorrhage by breaking down capillaries and affecting coagulation through depletion of coagulation factors in plasma (Moura-da-Silva et al. 2007).

Snake venom PLA2 enzymes are some of the most toxic proteins in venom, and they affect a multitude of physiological processes (Kini 2003). Most presynaptic neurotoxins in snake venoms are PLA2 or enzymes with PLA2 activity (Kini 2003; Gubenšek et al. 1997; Bon 1997). In addition, they have significant and wide ranging pharmacological effects like myotoxicity, hemolysis, cardiotoxicity and other organ and tissue damage. PLA2 family of enzymes hydrolyze substrate phospholipids and often act on a variety of pharmacological sites binding to target proteins. Penetrability of different svPLA2 enzymes also an important determinant in their ability to cause damage by hydrolysis.

β-bungarotoxins (β1 and β2) are PLA2-containing toxins that induce presynaptic toxicity by binding to nicotinic acetylcholine receptor and blocking the release of acetylcholine. (Cheng 2008).

Cobrotoxin is a short-chain non enzymatic basic protein in the three-finger toxin (3FT) family and is a major neurotoxin in the venom of *Naja atra* or Chinese Cobra (Yang 1999).

Snake venom serine proteases (SVSPs) (Serrano, 2013) are another important and ubiquitous class of venom proteins that are widely found in venoms of snakes from all families (except sea snakes where it is found more rarely) and geographies. Members of the SVSP toxin family show a great deal of substrate specificity and primarily affect the hemostatic system and affect various physiological functions like blood coagulation, fibrinolysis, blood pressure and platelet aggregation.

Antivenoms are currently the only recognized treatment for treating symptoms of snake bites. Conventional antivenoms are prepared by hyper-immunizing a large animal, generally a horse or a sheep, with snake venom to generate high affinity antibodies against immunogenic proteins in the snake venom. Horse serum is collected, and whole IgG molecules (150 kDa) are purified and used as whole IgG therapies, or are digested into F(ab')2 antibody fragments (100 kDa) or Fab antibody fragments (50 kDa) by pepsin or papain digestion respectively (Lalloo and Theakston 2003). These whole IgG antibodies, or antibody fragments are then administered intravenously to an envenomed patient to neutralize the activity of the snake venom toxins. Systemic envenomation generally can be treated with antivenom; administration of antivenom rapidly neutralizes neurotoxicity caused by the action of post-synaptic neurotoxins (Warrell 1992 cited in Gutierrez et al. 2006). However, traditional antivenom therapies come with a number of significant limitations. Introduction of animal serum or antibody products can cause adverse immune reactions in host resulting in anaphylaxis and serum sickness. Full-sized and fragment-formatted antibodies (Fab or F(ab)2) also do not penetrate tissue efficiently (Beckman et al. 2007) and therefore are not very effective in neutralizing toxins at distal sites. They are ineffective in treating local effects on tissues near the snake bite because of the rapid activity of the toxins at the local tissue, and the inability of antivenom immunoglobulin fragments to reach and penetrate deep tissues (Gutierrez et al. 1998). Although many survive envenomation, a large number of victims are left with chronic physical disability and psychological sequelae as a result of the cytotoxic components of the snake venom (Viravan et al. 1992).

Camelids (camels, llamas) have unique heavy chain only immunoglobulins devoid of light chains and the CH1 domains (Hamers-Casterman et al. 1993). The antigen binding sites of these heavy chain antibodies are composed of a single variable domain (called $V_H$H), and are the smallest natural antigen binding domain (15 kDa). $V_H$H antibody fragments have several properties that potentially make them superior candidates for antivenom development over traditional antibody-based antivenoms. They are relatively non-immunogenic, exhibit greater solubility and stability, and highly tissue penetrable (Arbabi Ghahroudi et al. 1997; Cortez-Retamozo et al. 2002 and 2004; Muruganandam et al., 2002). Owing to their low molecular mass, $V_H$H fragments permeate distal tissues more readily than conventional antibody fragments (Cortez-Retamozo et al., 2002 and 2004) and, therefore, may better protect victims from the tissuedamaging effects of venom toxins, both for acute effects on tissues and for venom effects that show up later due to tissue sequestration. Furthermore, because of their small size and high homology to the human VH3 gene family, $V_HHs$ may produce fewer adverse reactions in patients than conventional antivenoms (Vu et al., 1997). Furthermore, $V_HH$ antibody fragments can be easily expressed and purified from *E. coli*/yeast expression systems, solving the current short supply and high cost crisis of antivenoms (Arbabi Ghahroudi et al. 1997; Frenken et al. 2000).

SUMMARY OF THE INVENTION

The present invention provides camelid single heavy-chain antibody variable domains ($V_HH$) and related antigen-binding polypeptides that bind to snake venom proteins or peptides, pharmaceutical formulations of those $V_HH$, and associated methods for use, including for the treatment of envenomation. The invention also provides specific complementarity-determining regions (CDRs) and framework regions (FRs) from those $V_HH$.

In one aspect, the invention provides a $V_HH$ or antigen-binding polypeptide that binds to one or more (e.g., two, three, four, five, six, or more) snake venom proteins. In some embodiments, the $V_HH$ or antigen-binding polypeptide binds to two or more (e.g., two, three, four, five, six, or more) snake venom proteins from the same snake species. In other embodiments, the $V_HH$ or antigen-binding polypeptide binds to at least one snake venom protein from two or more (e.g., two, three, four, five, six, or more) snake species.

In some embodiments, the $V_HH$ or antigen-binding polypeptide binds to venom proteins from the same snake species, wherein the venom proteins are at least 70%, at least 75%, at least 80%, at least 85%, at least 90%, at least 95%, at least 99%, or 100% identical in their primary amino sequence. Alternatively, the $V_HH$ or antigen-binding polypeptide binds to unrelated venom proteins from same snake species (i.e., proteins that are less than 70% identical).

In some embodiments, the $V_HH$ or antigen-binding polypeptide binds to venom proteins from different snake species, wherein the venom proteins are at least 70%, at least 75%, at least 80%, at least 85%, at least 90%, at least 95%, at least 99%, or 100% identical in their primary amino sequence. Alternatively, the $V_HH$ binds to unrelated venom proteins from different snake species (i.e., proteins that are less than 70% identical).

In some embodiments, the snake venom protein(s) to which the $V_HH$ or antigen-binding polypeptide binds include one or more of snake venom metalloproteinase (SVMP), snake venom phospholipase A2 (svPLA2), snake venom serine protease (SVSP), cobrotoxin, and beta-bungarotoxin.

In some embodiments, the venomous snake species is *Agkistrodon piscivorus, Bungarus candidus, Calloselasma rhodostoma, Crotalus adamanteus, Crotalus atrox, Crotalus oreganus helleri, Crotalus scutulatus* (A), *Crotalus scutulatus* (B), *Deinagkistrodon acutus, Naja (Naja) siamensis, Naja (Naja) sputatrix* and *Ophiophagus hannah*, and any combination thereof. In some embodiments, the $V_HH$ or antigen-binding polypeptide binds to venom and/or venom proteins from snakes in the Viperidae and Elapidae families.

In some embodiments, the anti-svPLA2 $V_HH$ or antigen-binding polypeptide binds to the svPLA2 of North American crotalid species (e.g., *A. piscivorous, C. atrox, C. adamanteus, C. oreganus helleri*, and *C. scutulatus* (B)) and/or Asian crotalid species (e.g., *C. rhodostoma, D. acutus, D. russelli*, and *E. carinatus*) and/or Asian elapid species (e.g., *C. hannah*).

In some embodiments, the anti-beta-bungarotoxin $V_HH$ or antigen-binding polypeptide binds to North American crotalid species (e.g., *C. atrox*) and/or Asian crotalid species (e.g., *C. rhodostoma, D. acutus*, and *E. carinatus*) and/or Asian elapid species (e.g., *B. caerulus, B. candidus, N. kaouthia*, and *C. hannah*).

In some embodiments, the anti-SVMP $V_HH$ or antigen-binding polypeptide binds to North American crotalid species (e.g., *C. atrox*) and/or Asian crotalid species (e.g., *C. rhodostoma, D. acutus*, and *E. carinatus*) and/or Asian elapid species (e.g., *B. caerulus, B. candidus, N. kaouthia, N. siamensis, N. sputatrix*, and *C. hannah*).

In some embodiments, the $V_HH$ or antigen-binding polypeptide comprises an amino acid sequence selected from the group consisting of SEQ ID NO 1, SEQ ID NO 2, SEQ ID NO 3, SEQ ID NO 4, SEQ ID NO 5, and substantially identical sequences thereof (i.e., having at least 70%, at least 75%, at least 80%, at least 85%, at least 90%, at least 95%, or at least 99% sequence identity).

In some embodiments, the camelid from which the $V_HH$ is derived is a camel or llama.

In some embodiments, the isolated $V_HH$ or antigen-binding polypeptide binds to a venom protein that has enzymatic activity, and wherein $V_HH$ or antigen-binding polypeptide binding reduces or completely inhibits the activity of the enzyme. In some embodiments, the activity of the enzyme is reduced at least 30%, at least 40%, at least 50%, at least 60%, at least 70%, at least 80%, at least 90%, at least 95%, at least 99%, or 100%.

The invention also provides isolated CDRs and FRs derived from the $V_HHs$ of SEQ ID NOs: 1-5. In particular, the invention provides isolated CDR-1 regions provided as SEQ ID NOs: 6-10, isolated CDR-2 regions provided as SEQ ID NOs: 11-15, isolated CDR-3 regions provided as SEQ ID NOs: 16-20, FR-1 regions provided as SEQ ID NOs: 21-26, FR-2 regions provided as SEQ ID NOs: 27-32, FR-3 regions provided as SEQ ID NOs: 33-38, and FR-4 regions provided as SEQ ID NOs: 39-41, and variants that are substantially identical thereto (i.e., having at least 70%, at least 75%, at least 80%, at least 85%, at least 90%, at least 95%, or at least 99% sequence identity). The isolated CDRs and FRs may be used alone for any purpose or used to construct other venom protein-binding $V_HHs$ or antigen-binding polypeptides having the general formula: FR1-CDR1-FR2-CDR2-FR3-CDR3-FR4.

In another aspect, the invention provides a mixture of isolated $V_HH$ or antigen-binding polypeptides comprising two or more (e.g., three, four, five, six, seven, eight, or more) isolated $V_HH$ of the present invention.

In some embodiments, a single $V_HH$, antigen-binding polypeptide, or a mixture thereof is provided in a pharmaceutical formulation suitable for administration to a mammal (e.g., a human). Pharmaceutical formulations may include one or more $V_HH$, antigen-binding polypeptide, or pharmaceutically-acceptable salts thereof and a pharmaceutically-acceptable carrier. Pharmaceutical formulations may be formulated for oral, topical, or other parenteral administration including, for example, intravenous, intramuscular, and/or subcutaneous injection.

In another aspect, the invention also provides a method for treating envenomation of a mammal (e.g., a human) by administering a pharmaceutical formulation containing one or more (e.g., two, three, four, five, six, seven, eight, or more) $V_HH$ or antigen-binding polypeptides of the present invention. In some embodiments, the envenomation is caused by a snake species selected from the group consisting of *Agkistrodon piscivorus, Bungarus candidus, Calloselasma rhodostoma, Crotalus adamanteus, Crotalus atrox, Crotalus oreganus helleri, Crotalus scutulatus* (A), *Crotalus scutulatus* (B), *Deinagkistrodon acutus, Naja (Naja) siamensis, Naja (Naja) sputatrix* and *Ophiophagus Hannah*.

TABLE 1

Venom-binding V$_H$H

| SEQ ID NO: | Protein Binding Specificity (Designation) | Amino Acid Sequence | |
|---|---|---|---|
| 1 | Anti-SVMP (B6) | MAQVQLQESG GGLVAPGGSL RLSCAASENI RVKAMGWYRQ TPGKQRELVA | 50 |
| | | TISARPSGGI TNYVDPVKGR FTISRDNAKN VLYLQMNSLK PEDTGVYYCN | 100 |
| | | IVGTNIWGQG TQVTVSSTSG PGGQHHHHHH GAEQKLISEE DLS | 143 |
| 2 | Anti-SVMP (D11) | MAQVQLQESG GGLVQAGGSL RLSCAASGRT FSSAAMGWFR RAPGEEREFV | 50 |
| | | AAISWSGGTT HYTESVKGRF TISRDNAKNT VSLQMDSLKP EDTAIYYCAA | 100 |
| | | DMALSTVVEG TSRYWGQGTQ VTVSSTSGPG GQHHHHHHGA EQKLISEEDL | 150 |
| | | S | 151 |
| 3 | Anti-bungarotoxin (A4) | MAQVQLQESG GGLVQAGDSL RLSCAASGHT FRDRAMNWFR QAPGKEREFV | 50 |
| | | AAIHWSDGRT FYTDSVKGRF TISRDNAKNT GYLQMNSLKT EDTAVYYCAI | 100 |
| | | VMAYPWTTPG GINDWGKGTL VTVSSTSGPG GQHHHHHHGA EQKLISEEDL | 150 |
| | | S | 151 |
| 4 | Anti-cobrotoxin (B9) | MAQVQLQESG GGLAQAGGSL RLSCSASRNI FRVYGWYRQA PGKQREWVAS | 50 |
| | | ITRDDSTAYA DSVKGRFTIS RDSAKNTMYL QMSSLRLEDT STYYCAAQSI | 100 |
| | | SGTIQWGQGT QVTVSSTSGP GGQHHHHHHG AEQKLISEED LS | 142 |
| 5 | Anti-PLA2 (H3) | LAQVQLQQSG GGLVQAGDSL RLSCAASGRT FRDRAMNWFR QAPGKEREFV | 50 |
| | | AAIHWSDGRT YYADSVKGRF TISRDNAKNT GSLQMDSLKT EDTGVYYCAI | 100 |
| | | VMAYPWTTPG GINDWGKGTL VTVSSTSGPG GQHHHHHHGA EQKLISEEDL | 150 |
| | | S | 151 |

TABLE 2

Exemplary CDR-1 Domains From Venom-binding V$_H$H

| SEQ ID NO: | V$_H$H | Amino Acid Sequence |
|---|---|---|
| 6 | B6 | ENIRVKA |
| 7 | D11 | GRTFSSAA |
| 8 | A4 | GHTFRDRA |
| 9 | B9 | RNIFRV |
| 10 | H3 | GRTFRDRA |

TABLE 3

Exemplary CDR-2 Domains From Venom-binding V$_H$H

| SEQ ID NO: | V$_H$H | Amino Acid Sequence |
|---|---|---|
| 11 | B6 | ISARPSGGIT |
| 12 | D11 | ISWSGGTT |
| 13 | A4 | IHWSDGRT |
| 14 | B9 | ITRDDST |
| 15 | H3 | IHWSDGRT |

TABLE 4

Exemplary CDR-3 Domains From Venom-binding V$_H$H

| SEQ ID NO: | V$_H$H | Amino Acid Sequence |
|---|---|---|
| 16 | B6 | NIVGTNI |
| 17 | D11 | AADMALSTVVEGTSRY |
| 18 | A4 | AIVMAYPWTTPGGIND |
| 19 | B9 | AAQSISGTIQ |
| 20 | H3 | AIVMAYPWTTPGGIND |

TABLE 5

Exemplary FR-1 Domains From Venom-binding V$_H$H

| SEQ ID NO: | V$_H$H | Amino Acid Sequence |
|---|---|---|
| 21 | B6 | MAQVQLQESGGGLVAPGGSLRLSCAAS |
| 22 | D11 | MAQVQLQESGGGLVQAGGSLRLSCAAS |
| 23 | A4 | MAQVQLQESGGGLVQAGDSLRLSCAAS |
| 24 | B9 | MAQVQLQESGGGLAQAGGSLRLSCSAS |
| 25 | H3 | LAQVQLQQSGGGLVQAGDSLRLSCAAS |
| 26 | Consensus | (M/L)AQVQLQ(Q/E)SGGGL(V/A) (Q/A)G(G/D)SLRLSC(S/A)AS |

TABLE 6

Exemplary FR-2 Domains From Venom-binding $V_HH$

| SEQ ID NO: | $V_HH$ | Amino Acid Sequence |
|---|---|---|
| 27 | B6 | MGWYRQTPGKQRELVAT |
| 28 | D11 | MGWFRRAPGEEREFVAA |
| 29 | A4 | MNWFRQAPGKEREFVAA |
| 30 | B9 | YGWYRQAPGKQREWVAS |
| 31 | H3 | MNWFRQAPGKEREFVAA |
| 32 | Consensus | (M/Y)(G/N)W(F/Y)R(R/Q)(A/T)PG(K/E)(Q/E)RE(F/L/W)VA(A/S/T) |

TABLE 7

Exemplary FR-3 Domains From Venom-binding $V_HH$

| SEQ ID NO: | $V_HH$ | Amino Acid Sequence |
|---|---|---|
| 33 | B6 | NYVDPVKGRFTISRDNAKNVLYLQMNSLKPEDTGVYYC |
| 34 | D11 | HYTESVKGRFTISRDNAKNTVSLQMDSLKPEDTAIYYC |
| 35 | A4 | FYTDSVKGRFTISRDNAKNTGYLQMNSLKTEDTAVYYC |
| 36 | B9 | AYADSVKGRFTISRDSAKNTMYLQMSSLRLEDTSTYYC |
| 37 | H3 | YYADSVKGRFTISRDNAKNTGSLQMDSLKTEDTGVYYC |
| 38 | Consensus 1 | (A/F/H/N/Y)Y(A/T/V)(D/E)(S/P)VKGRFTISRD(N/S)AKN(T/V)(G/L/M/V)(S/Y)LQM(D/N/S)SL(K/R)(L/P/T)EDT(A/G/S)(I/T/V)YYC |

TABLE 8

Exemplary FR-4 Domains From Venom-binding $V_HH$

| SEQ ID NO: | $V_HH$ | Amino Acid Sequence |
|---|---|---|
| 39 | B6, D11, B9 | WGQGTQVTVSSTSGPGGQHHHHHGAEQKLISEEDLS |
| 40 | A4, H3 | WGKGTLVTVSSTSGPGGQHHHHHGAEQKLISEEDLS |
| 41 | Consensus | WG(K/Q)GT(L/Q)VTVSSTSGPGGQHHHHHHGAEQKLISEEDLS |

The present disclosure also includes variants of the isolated $V_HH$ that can bind to one or more of the same proteins or peptides present in venom recognized by the isolated $V_HH$ disclosed above. The term "variant" as used herein includes modifications or chemical equivalents of the amino acid sequences disclosed herein that perform substantially the same function as the isolated $V_HH$ disclosed herein in substantially the same way. For example, variants of amino acid sequences disclosed herein include, without limitation, conservative amino acid substitutions. A "conservative amino acid substitution" as used herein, is one in which one amino acid residue is replaced with another amino acid residue without abolishing the binding properties of the isolated $V_HH$s. Examples of conservative substitutions include the substitution of one non-polar (hydrophobic) residue such as alanine, isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

As used herein, the term "$V_HH$" refers to a variable domain of a camelid heavy-chain antibody.

As used herein, the term "isolated $V_HH$" refers to a $V_HH$ which has been separated from a component of its natural environment. vThe term "camelid" as used herein means a member of the family Camelidae including, without limitation, llamas, camels, dromedaries, alpacas, vicunas and guanacos.

The "binding affinity" of an antibody is the strength of binding of a monovalent ligand to a single antigen-binding site on the antibody, which may be measured methods known in the art such as ELISA, enzyme-linked immuno-spot (Elispot), immunofluorescence, and immunoelectrophoresis.

An isolated $V_HH$ is "stable" if it shows no significant increase of aggregation, precipitation and/or denaturation upon visual examination of color and/or clarity, or as measured by UV light scattering, gel electrophoresis of protein, size exclusion chromatography (SEC) and dynamic light scattering (DLS).

The term "envenomation" refers to injection of venom into a victim as a result of a bite or a sting by a reptile, amphibian, arthropod, mollusk, cnidarian, insect, coelenterate or other venomous vertebrate or invertebrate animal.

The terms "treat", "treating", and "treatment", are used synonymously to refer to any action providing a benefit to a subject (i.e., a mammal, particularly a human) suffering from an envenomation, including improvement in the condition through lessening, inhibition, suppression or elimination of at least one symptom, delay in progression of or damage from the envenomation or related condition, prevention, delay in or inhibition of the likelihood of the onset of envenomation symptoms, etc.

BRIEF DESCRIPTION OF THE DRAWINGS

FIG. 5: Binding of lead purified V$_H$H candidates to venoms of different snake species determined by ELISA.

DETAILED DESCRIPTION

The invention provides compositions and associated reagents, and related methods for treating snake envenomation in humans and animals. Disclosed herein are novel V$_H$H that bind to snake venom proteins and other toxins/molecules, along with an identification of the complementarity-determining and framework regions contained therein. Thus, the invention provides the specific V$_H$H and novel V$_H$H that may be constructed by assembling a V$_H$H according to the general formula FR1-CDR1-FR2-CDR2-FR3-CDR3-FR4 from the component domains described herein.

I. Construction of V$_H$H Antibody Fragment Library

A phage-displayed V$_H$H library was constructed from a llama hyperimmunized with the crude venoms of twelve medically relevant species (Table 9) with distinct toxin compositions. Venom from each species constitutes 1/12th of the total immunization mixture by volume. This method was chosen to generate high diversity in the library and to ultimately obtain high affinity binders to a wide range of snake venom toxins.

Table 1. Venomous snake species contributing to crude venom immunization mixture in generation of V$_H$H antibody fragment library.

TABLE 9

| Snake Species Contributing Crude Venom To Immunization Mixture | |
|---|---|
| Scientific Name | Common Name |
| Agkistrodon piscivorus | Water moccasin; cottonmouth |
| Bungarus candidus | Blue krait |
| Calloselasma rhodostoma | Malayan pit viper |
| Crotalus adamanteus | Eastern diamondback rattlesnake |
| Crotalus atrox | Western diamondback rattlesnake |
| Crotalus oreganus helleri | Southern pacific rattlesnake |
| Crotalus scutulatus (A) | Mojave rattlesnake (Toxin Type A) |
| Crotalus scutulatus (B) | Mojave rattlesnake (Toxin Type B) |
| Deinagkistrodon acutus | Sharp nosed pit viper |
| Naja (Naja) siamensis | Indochinese Cobra |
| Naja (Naja) sputatrix | Javan spitting cobra |
| Ophiophagus Hannah | King cobra |

Figure 1:
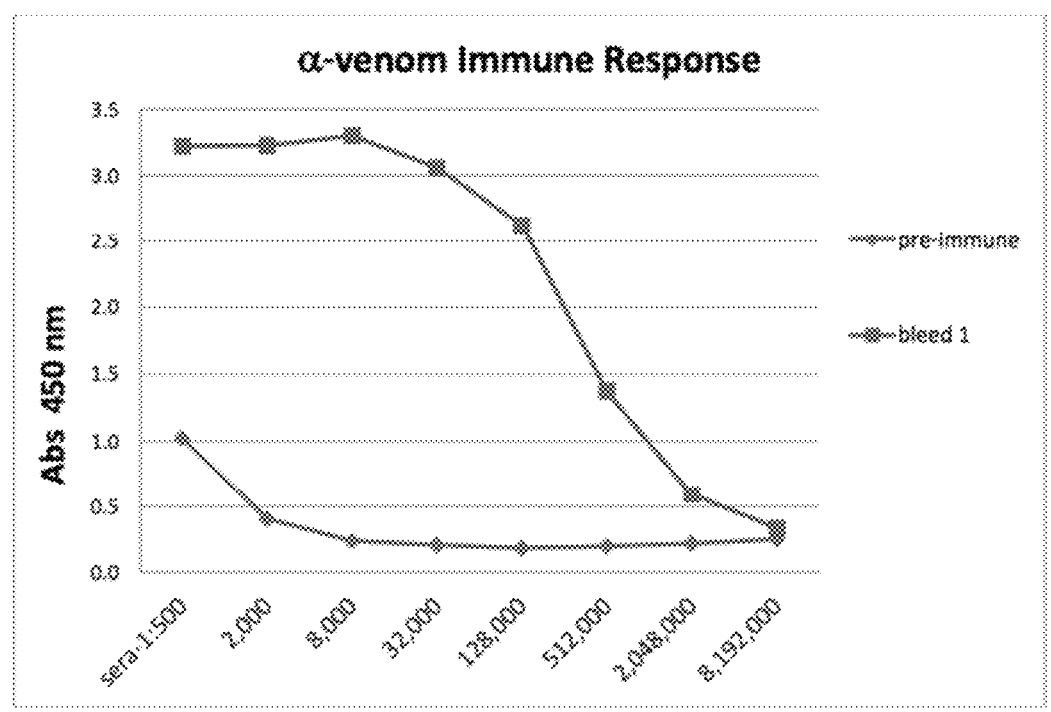
FIG. 1: Representative ELISA data comparing llama serum titers of venom-binding antibodies (including single-domain antibodies) between pre-immunization bleed (tilted square tracer) with post-immunization bleed (post-immunization bleed 1; square tracer) at different serum dilutions.

The llama was immunized over a period of approximately 17 weeks with bleeds taken at three points during the schedule (Table 10). The serum titers from each of these bleeds were assayed for immune response to the immunization mixture using ELISA (FIG. 1). FIG. 1 demonstrates increased binding of llama serum titers of venom-binding antibodies (including single-domain antibodies) with post-immunization bleed (post-immunization bleed 1; square tracer) as compared to pre-immunization bleed (tilted square tracer) at different serum dilutions.

TABLE 10

| Llama Immunization Schedule | | | | |
|---|---|---|---|---|
| Day | Procedure | Dose (mg) | Adjuvant | Endpoints |
| 0 | Pre-Immune Bleed | | | ELISA/PBMC |
| 5 | Immunization 1 | 0.25 | CFA | |
| 20 | Immunization 2 | 0.5 | IFA | |
| 40 | Immunization 3 | 0.75 | IFA | |
| 47 | Bleed 1 | | | ELISA/PBMC |
| 61 | Immunization 4 | 1 | IFA | |
| 78 | Immunization 5 | 1.25 | IFA | |
| 85 | Bleed 2 | | | ELISA/PBMC |
| 96 | Immunization 6 | 1.5 | IFA | |
| 119 | Immunization 7 | 2 | IFA | |
| 126 | Bleed 3 | | | ELISA/PBMC |

Figure 2:
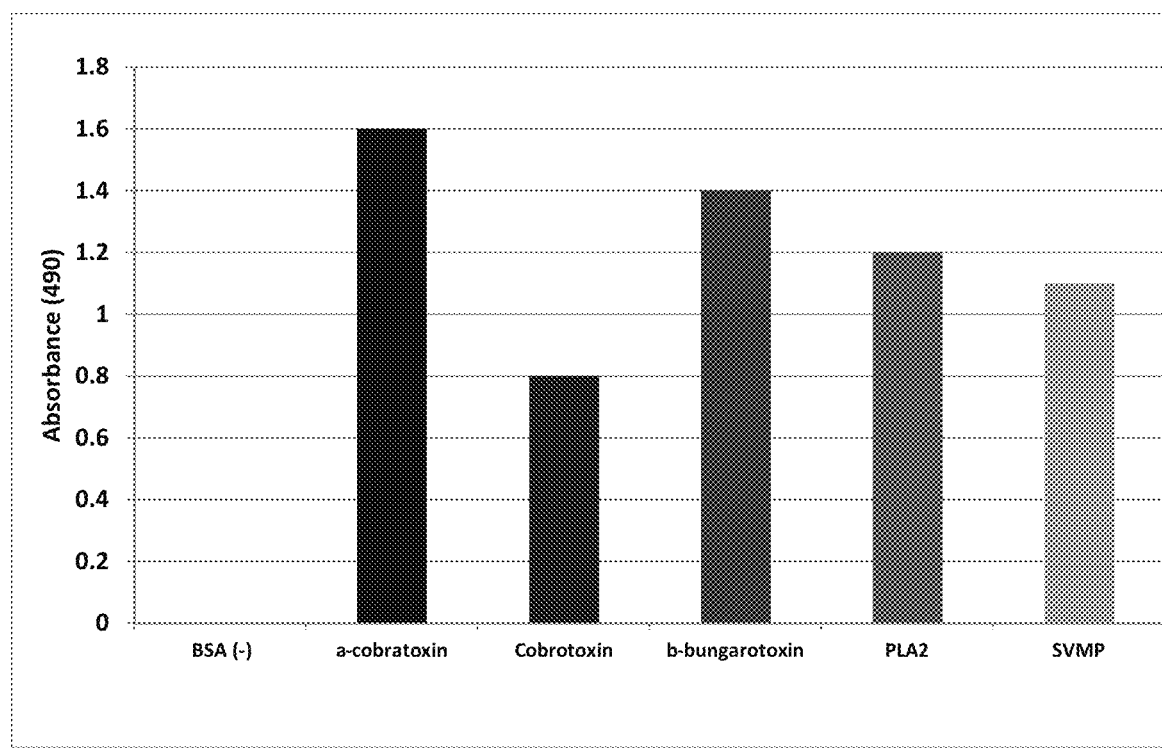
FIG. 2: ELISAs showing binding of post-immunized llama serum to purified α-cobratoxin, Cobrotoxin, β-Bungarotoxin, PLA2, and SVMP.

ELISA results show binding of post-immunized llama serum to purified toxins: α-cobratoxin, Cobrotoxin, β-Bungarotoxin, PLA2, and SVMP (FIG. 2). The results demonstrate that the post-immunized llama serum contains antibodies against these toxins. As a control, BSA protein is used and the post-immunized llama serum does not bind to BSA showing that the serum has overabundance of toxin-specific antibodies.

II. Anti-Snake Venom Metalloproteinase (SVMP)

Purified, lyophilized snake venom metalloproteinase (SVMP) from Crotalus atrox venom was obtained from the National Natural Toxin Research Center (Kingsville, Tex.) and reconstituted in phosphate buffered saline (PBS, pH 7.4) to a final concentration of 1 mg/ml. This was stored in 20 µl aliquots at −20° C., and used in all subsequent panning, ELISA and in vitro protease assay experiments.

Panning for SVMP-Binding V$_H$H Antibodies

Panning procedures using a V$_H$H library generated from one venom-immunized Llama (see section I for immunogen formulation and immunization schedule) were performed according to well-established procedures described elsewhere with minor modifications. Briefly, a single well of a 96-well microtiter plate (Nunc Maxisorp, Thermofisher, CA USA) was coated with 100 µl of SVMP (0.1 mg/ml in PBS) for 2 hours at 4° C. The coating solution was removed, and the wells blocked with 250 µl of PBS-TB blocking solution (PBS, 0.05% Tween-20, 2% BSA) overnight at 4° C. The blocking solution was removed, and 1011 V$_H$H-phages were added to the well, which was then incubated at 37° C. for 1 hour. The well was washed 10 times with PBS (250 µl), then a further 3 times with PBS containing 0.1% Tween-20, and bound phages were eluted with 100 µl of a solution containing 0.2 M Glycine (pH 2.2), 1 mg/ml BSA. The eluted phages were used to infect 400 µl of a log-phase E coli (TG1) culture for library amplification, or plated on 2XTY agar plates containing 50 µg/ml carbenicillin and 2% glucose and incubated overnight at 37° C.

Screening for SVMP-Specific V$_H$H Antibodies

Screening for SVMP-specific V$_H$H antibodies was carried out by phage ELISA according to procedures described elsewhere. Briefly, individual colonies of V$_H$H-phagemid transformed TG1 cells were inoculated into the wells of round-bottom, 96-well microtiter plate containing 100 µl of 2XTY medium supplemented with 50 µg/ml carbenicillin and 2% glucose (2XTYBG). The plate was incubated with shaking (200 rpm) overnight at 37° C. 100 of the overnight cultures were transferred to 90 µl of fresh 2XTYBG dispensed into the wells of a fresh microtiter plate, and the cultures incubated at 37° C. for a further 1-2 hours (until the OD600 reached approximately 0.6). The remaining cultures were used to make master stocks by adding glycerol to a final concentration of 15%—these were stored at −80° C.

1011 helper phages (M13K07, Antibody Design Labs, CA USA) were added to each well of the log-phase cultures, and the plate was incubated at 37° C. with shaking for 1 hr. The plate was centrifuged at 3000×g for 15 minutes, the supernatants removed and the cell pellets resuspended in 150 μl of fresh 2XTY medium containing 50 μg/ml carbenicillin and 50 μg/ml of kanamycin (2XTYCK). This was incubated at 30° C. overnight with shaking.

After overnight incubation, the plate was centrifuged at 3000×g for 15 minutes, and the supernatants carefully removed and dispensed into a fresh 96-well microtiter plate. The presence of SVMP-binding $V_HH$-phages in the cell culture supernatants was then tested by phage ELISA according to well-established procedures. Briefly, a 96-well Maxisorp microtiter plate was coated with purified SVMP (1 μg/ml in PBS) and blocked with PBS-TB as described in section II(i). After removing the blocking solution, 50 μl of each supernatant was added to the SVMP-coated wells, and the plate was incubated at 37° C. for 1 hour. After washing 5 times with 300 μl of PBS containing 0.05% Tween-20 (PBS-T)—the standard ELISA washing procedure—the wells were probed with 100 μl of an anti-M13 phage antibody (Antibody Design Labs, CA USA; 1 μg/ml) for 1 hour at room temperature. The wells were washed, incubated with 100 μl of an HRP-conjugated secondary mouse antibody (1 μg/ml, Thermofisher), washed again, and bound phages detected colorimetrically following incubation with 50 μl of TMB Ultra ELISA substrate (Thermofisher).

Sequencing of SVMP-Binding $V_HH$ Antibodies.

Clones producing SVMP-binding $V_HH$-phages were selected and cultured by inoculating 5 μl of $V_HH$-phage expressing glycerol stock into 150 μl of 2XTYCG medium pre-dispensed into the wells of a 96-well round-bottom microtiter plate. The plate was incubated at 37° C. for 16 hours with shaking, and frozen at −80° C. prior to direct sequencing of $V_HH$-encoding cassettes using a phi-S2 primer (ATGAAATACCTATTGCCTACGG; SEQ ID NO: 41). Sequencing was performed by Quintara Biosciences (San Francisco, Calif. USA).

Purification of SVMP-Binding $V_HH$ Antibodies

5 μl of TG1 glycerol stocks containing SVMP-binding, $V_HH$-encoding phagemid were inoculated into 5 ml of 2XTYCG medium, which was incubated at 37° C. for 16 hours with shaking (250 rpm). Recombinant $V_HH$-expressing phagemids were isolated from the overnight cultures by standard plasmid extraction procedures. These were used to transform SS320 E. coli, a non-suppressor of amber stop codons enabling direct phagemid-based $V_HH$ expression and secretion. Briefly, single colonies of transformed SS320 cells were inoculated into 100 ml of 2XTY medium containing 50 μg/ml of carbenicillin (2XTYC), which was incubated at 37° C. with shaking (250 rpm) until the culture OD600 reached approximately 0.6. Isopropyl β-D-1-thiogalactopyranoside (IPTG) was added to each culture to a final concentration of 1 mM, and these were incubated for a further 16 hours with shaking at 25° C. Expressed $V_HH$ antibodies were purified from isolated periplasmic fractions by affinity chromatography according to well-established procedures described elsewhere. The purity and integrity of purified $V_HH$s was analyzed by SDS-PAGE and Western Blotting.

$V_HH$-SVMP Binding ELISA Assay

Binding of purified $V_HH$s to SVMP was assessed by ELISA according to methods outlined in section II(ii), with the following modifications. Following coating of 96-well Maxisorp microtiter plates with SVMP (1 μg/ml) or crude snake venom (5 μg/ml) and blocking with PBS-TB, wells were incubated with purified $V_HH$ samples (1 μg/ml in PBS-T) for 1 hour at 37° C. After washing by standard procedures (5×, 300 PBS-T), bound $V_HH$ was incubated with an HRP-conjugated his-tag-binding probe (HisProbe, 0.5 μg/ml, ThermoFisher, CA USA), and detected colorimetrically by standard methods.

In Vitro Protease Inhibition Assay

The ability of purified $V_HH$s to inhibit SVMP activity was assessed in vitro by azo-casein proteolysis assay. This analysis relies on the protease-dependent release of azo dye into solution following digestion of substrate azo-casein conjugates. 60 ul reactions containing purified SVMP (0.05-0.5 mg/ml), $V_HH$ (0.5-0.1 mg/ml) and azo-casein (10 mg/ml) in 50 mM Tris 150 mM NaCl, 5 mM CaCl2 (pH 8.0) were set up and incubated at 37° C. for 2 hours. Control reactions did not contain $V_HH$, and reference reactions did not contain SVMP. The reactions were stopped with 100 ul of a 5% trichloroacetic acid solution, and then centrifuged at 12000×g for 5 minutes at room temperature. The supernatant (100 ul) was removed carefully and neutralized with 100 ul of 0.5 M NaOH before measuring the absorbances at 490 nm.

Amino acid sequences of lead purified $V_HH$ candidates binding to SVMP are shown in Table 1 and provided as SEQ ID NOs: 1-5.

III. Generation of $V_HH$ Antibodies Against svPLA2, β-Bungarotoxin, and Cobrotoxin $V_HH$ antibodies targeting svPLA2, β-bungarotoxin, and cobrotoxin were generated by following the same procedures described in section II (i-v), using the following purified proteins (reconstituted to 1 mg/ml in PBS) for panning and post-panning analysis: PLA2 (C. adamanteus, Worthington Labs; C. rhodostoma, Venomtech, Inc.); β-bungarotoxin (B. multicentis, Miami Serpentarium, FL USA); Cobrotoxin (N. Atra, Miami Serpentarium, FL USA).

Amino acid sequences of lead purified $V_HH$ candidates binding to PLA2, β-bungarotoxin, and cobrotoxin are shown in Table 1 above.

IV. Binding of Lead Purified $V_HH$ Candidates to Venoms of Different Snake Species Binding of lead purified $V_HH$ candidates against different toxins, i.e., PLA2, β-bungarotoxin, cobrotoxin and SVMP, were tested for venoms of different snake species using ELISA (FIG. 5). The numbers and the density of shading is indicative of strength of binding compared with a negative control BSA. "x" indicates that these combinations have not been tested yet. The $V_HH$ candidate against PLA2 showed binding to at least 10 out of 18 venoms of different snake species. Similarly, the $V_HH$ candidate against β-bungarotoxin showed binding to at least 10 out of 18 venoms of different snake species. The $V_HH$ candidate against cobrotoxin showed binding to at least 6 out of 11 venoms of different snake species. The $V_HH$ candidate against SVMP showed binding to at least 8 out of 11 venoms of different snake species. These results demonstrate that the purified $V_HH$ candidates are capable of binding to venoms of different snake species.

The disclosed embodiments are susceptible to various modifications and alternative forms, and specific examples thereof have been shown by way of example in the drawings and are herein described in detail. It should be understood, however, that the disclosed embodiments are not to be limited to the particular forms or methods disclosed, but to the contrary, the disclosed embodiments are to cover all modifications, equivalents, and alternatives.

V. Cross Species Neutralization of PLA2 Activity by a Lead Purified $V_HH$ Candidate against PLA2

Figure 3:
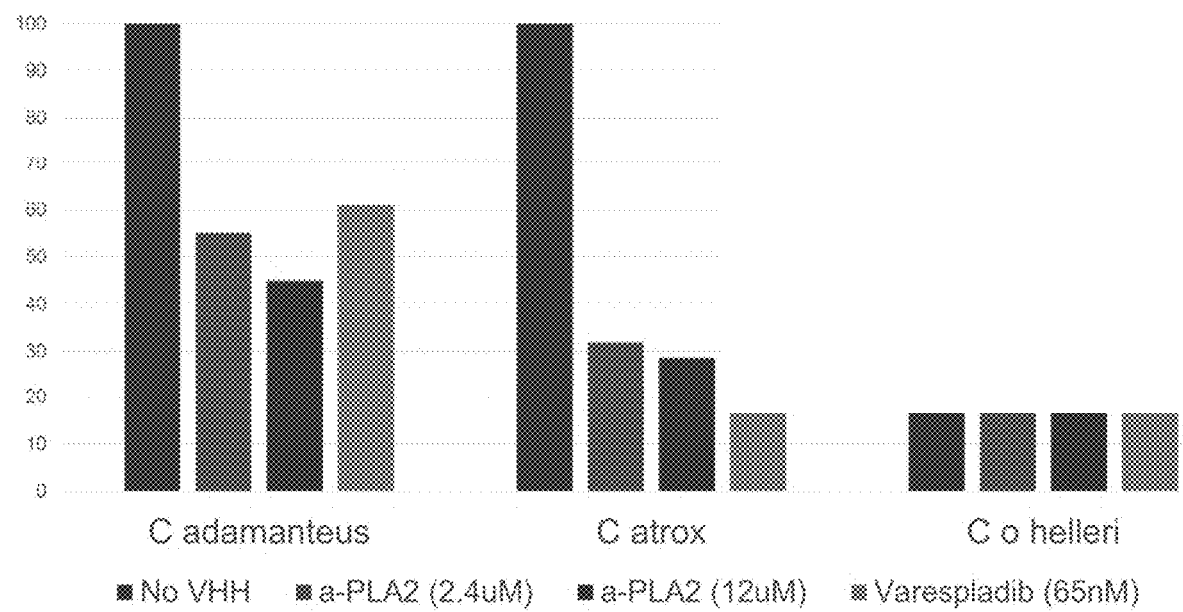
FIG. 3: Enzymatic assay data showing in vitro neutralization of PLA2 activity on venoms of three different snake species by the anti-PLA2 purified $V_HH$ candidate. The y-axis shows percent PLA2 activity. On the x-axis three different snake species are shown: *Crotalus adamanteus*, *Crotalus atrox* and *Crotalus oreganus helleri*. For each snake species, the four bars from left to right represent (1) no $V_HH$, (2) anti-PLA2 $V_HH$ (2.4 µM), (3) anti-PLA2 (12 µM) and (4) Varespladib (65 µM).

An in vitro enzymatic assay for the lead purified $V_HH$ candidate against PLA2 was performed to test neutralization of PLA2 activity on venoms of three different snake species:

*Crotalus adamanteus, Crotalus atrox* and *Crotalus oreganus helleri* (FIG. 3). In FIG. 3, the y-axis shows percent PLA2 activity. On the x-axis three different snake species are shown: *C. adamanteus, C. atrox* and *C. oreganus helleri*. For each snake species, the four bars from left to right represent (1) no $V_HH$, (2) anti-PLA2 $V_HH$ (2.4 µM), (3) anti-PLA2 (12 µM) and (4) Varespladib (65 µM). Varespladib is a small molecule inhibitor of PLA2 and is used as a positive control.

As shown in FIG. 3, both concentrations (2.4 µM and 12 µM) of the lead purified $V_HH$ candidate against PLA2 reduced PLA2 activity in all three species as compared to control. These results demonstrate that the lead purified $V_HH$ candidate against PLA2 is capable of cross species neutralization of PLA2 activity.

VI. Stability of Lead Purified $V_HH$ Candidate against PLA2

Figure 4:
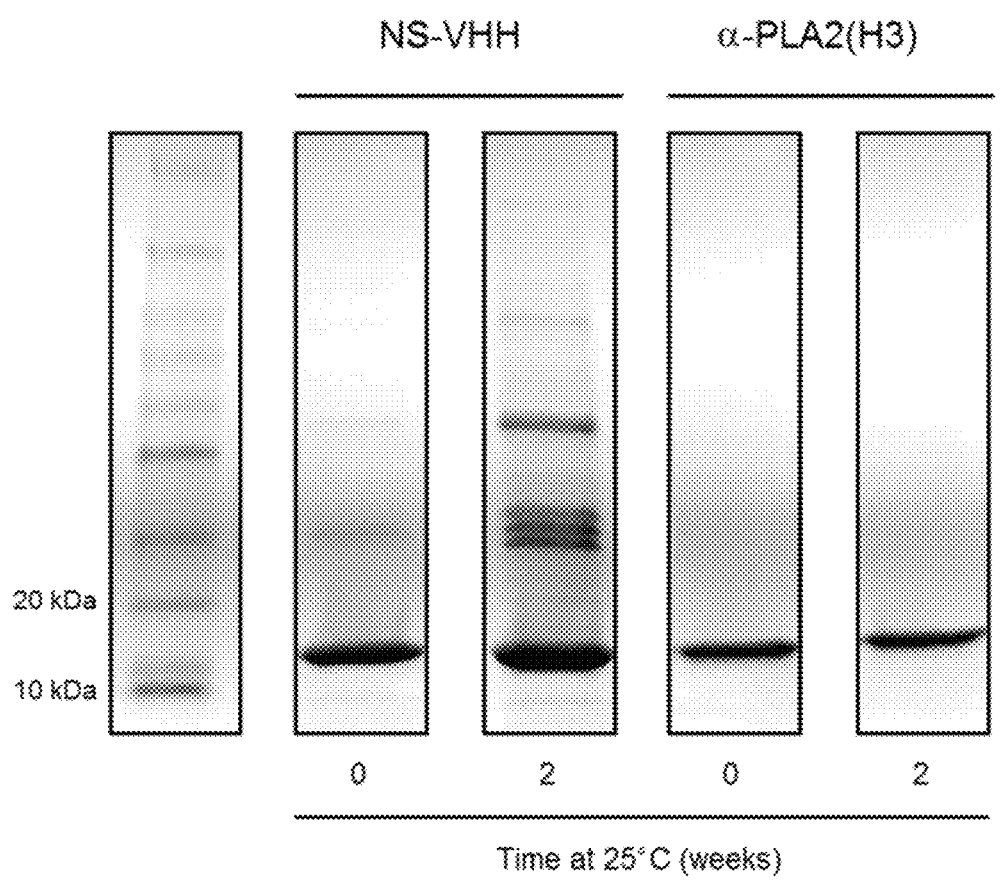
FIG. 4. Representative data showing stability of anti-PLA2 purified V$_H$H candidate.

In order to test the stability of lead purified $V_HH$ candidates, a non-specific (NS) $V_HH$ candidate and an anti-PLA2 $V_HH$ candidate were left in room temperature (25° C.) for two weeks. FIG. 4 demonstrated that after two weeks in room temperature the NS $V_HH$ candidate exhibited multiple bands above 20 kDa as compared to the anti-PLA2 $V_HH$ candidate which had only a single major band at the expected molecular weight (15 kDa). The multiple bands of higher molecular weight suggest substantial aggregation of the NS $V_HH$ candidate. The results indicate that there was substantial change in stability for the NS $V_HH$ candidate. These findings suggest that stability varies among different $V_HH$ antibodies.

REFERENCES

Arbabi Ghahroudi, M., Desmyter, A., Wyns, L., Hamers, R., Muyldermans, S. 1997. Selection and identification of single domain antibody fragments from camel heavy-chain antibodies. FEBS Lett. 414:521-526.

Beckman R A, Weiner L M, Davis H M. 2007. Antibody constructs in cancer therapy: protein engineering strategies to improve exposure in solid tumors. Cancer. 109:170-179.

Bourne, Y., Talley, T. T., Hansen, S. B., Taylor, P., Marchot, P. 2005. Crystal structure of α-Cbtx-AChBP complex reveals essential interactions between snake α-neurotoxins and nicotinic receptors. EMBO J. 24:1512-1522.

Bulbring, E. 1946. Observation on the isolated phrenic nerve-diaphragm preparation of the rat. Br. J. Pharmacol. 1: 38-61.

Calvete, J. J.; Sanz, L.; Angulo, Y.; Lomonte, B.; Gutierrez, J. M. 2009. Venoms, venomics, antivenomics. FEBS Lett. 583:1736-1743.

Cheng Y. C., Wang J. J., Chang, L. S. 2008. B chain is a functional subunit of beta-bungarotoxin for inducing apoptotic death of human neuroblastoma SK-N-SH cells". Toxicon. 51 (2): 304-15

Chippaux, J. P. 1998. Snake-bites: appraisal of the global situation. Bull. World Health Organ. 76:515-524.

Chippaux, J. P. 2006. The Epidemiology of Envenomations. In Snake venoms and envenomations. Translated by F. W. Huchzermeyer. Krieger Publishing Company, Florida. pp. 193.

Chotwiwatthanakun, C., Pratanaphon, R., Akesowan, S., Sriprapat, S., Ratanabanangkoon, K. 2001. Production of potent polyvalent antivenom against three elapid venoms using a low dose, low volume, multi-site immunization protocol. Toxicon. 39: 1487-1494.

Cortez-Retamozo, V., Lauwereys, M., Hassanzadeh, G. H., Gobert, M., Conrath, K., Muyldermans, S., De Baetselier, P., Revets, H. 2002. Efficient tumor targeting by single-domain antibody fragments of camels. Int. J. Cancer. 98:456-462.

Cortez-Retamozo, V., Backmann, N., Senter, P. D., Wernery, U., De Baetselier, P., Muyldermans, S., Revets, H. 2004. Efficient cancer therapy with a nanobody-based conjugate. Cancer Res. 64: 2853-2857.

Frenken, L., van der Linden, R. H. J., Hermans, P. W. J. J. 2000. Isolation of antigen-specific Llama $V_HH$ antibody fragment and their high level of secretion by Saccharomyces cerevisiae. 78:11-21.

Ghahroudi, M. A, Desmyter, A., Wyns, L., Hamers, R., Muyldermans, S. 1997. Selection and identification of single domain antibody fragments from camel heavy-chain antibodies. FEBS Letters. 414: 521-526.

Gutierrez J M, Theakston R D, Warrell D A. Confronting the neglected problem of snake bite envenoming: the need for a global partnership. PLoS Med 2006; 3:e150.

Gutierrez, J. M., Leon, G., Rojas, G., Lamonte, B., Rucavado, A., Chaves, F. 1998. Neutralization of local tissue damage induced by Bothrops asper (terciopelo) snake venom. Toxicon. 36:1529-1536.

Gutierrez, J. M., Rucavado, A. 2000. Snake venom metalloproteinases: Their role in pathogenesis of local tissue damage. Biochimie 82:841-850.

Hamers-Casterman, C., Atarhouch, T., Muyldermans, S., Robinson, G., Hamer, C., Songa, E. B., Bendahman, N.; Hamers, R. 1993. Naturally occurring antibodies devoid of light chains. Nature. 363:446-448.

Harmsen M. M., Ruuls R. C., Nijman I. J., Niewold T. A., Frenken L. G. and de Geus B. 2000. Llama heavy-chain V regions consist of at least four distinct subfamilies revealing novel sequence features. Mol Immunol 37, 579-90.

Harrison R A, Hargreaves A, Wagstaff S C, Faragher B, Lalloo D G. Snake envenoming: a disease of poverty. PLoS Negl Trop Dis 2009; 3:e569.

Inoue, S., Ohkura, K., Ikeda, K., Hayashi, K. 1987. Amino acid sequence of a cytotoxin-like basic protein with low cytotoxic activity from the venom of the Thailand cobra Naja naja siamensis. FEBS 218:17-21.

Kabat E. A. and Wu T. T. 1991. Identical V region amino acid sequences and segments of sequences in antibodies of different specificities. Relative contributions of VH and VL genes, minigenes, and complementarity-determining regions to binding of antibody-combining sites. J Immunol 147, 1709-19.

Karlsson, E. 1979. Chemistry of protein toxins in snake venoms. In Handbook of Experimental Pharmacology. Edited by C. Y. Lee. Springer, Berlin, 52:159-212.

Lalloo, D., Theakston, R. D. 2003. Snake antivenoms. J. Toxicol. Clin. Toxicol. 41:277-290.

Minton, S. A. 1990. Neurotoxic snake envenoming. Semin. Neurol. 10: 52-61.

Moura-da-Silva, A. M.; Butera, D.; Tanjoni, I. 2007. Importance of snake venom metalloproteinases in cell biology: Effects on platelets, inflammatory and endothelial cells. Curr. Pharm. Des. 2007, 13:2893-2905.

Moura-da-Silva, A. M, Almeida, M. T., Portes-Junior, J. A., Nicolau, C. A., Gomes-Neto, F., Valente, R. H. 2016 Processing of Snake Venom Metalloproteinases: Generation of Toxin Diversity and Enzyme Inactivation Toxins. Toxins 8(6), 183

Muruganandam, A., Tanha, J., Narang, S., Stanimirovic, D. 2002. Selection of phage-displayed llama single-domain antibodies that transmigrate across human blood-brain barrier endothelium. FASEB J. 16: 240-242.

Pratanaphon, R., Akesowan, S., Khow, O., Sriprapat, S., Ratanabanangkoon, K. 1997. Production of highly potent horse antivenom against the Thai cobra (Naja kaouthia). Vaccine. 15:1523-1528.

Serrano, S. M. 2013. The long road of research on snake venom serine proteinases. Toxicon. 62:19-26

Sousa, L. F.; Nicolau, C. A.; Peixoto, P. S.; Bernardoni, J. L.; Oliveira, S. S.; Portes-Junior, J. A.; Mourão, R. H.; Lima-dos-Santos, I.; Sano-Martins, I. S.; Chalkidis, H. M.; Valente, R. H.; Moura-da-Silva, A. M. 2013. Comparison of phylogeny, venom composition and neutralization by antivenom in diverse species of bothrops complex. PLoS Negl. Trop. Dis. 7(9):e2442.

Stewart, C. S., MacKenzie, R. C., Hall, J. C. 2007. Isolation, characterization and pentamerization of α-cobrotoxin specific single-domain antibodies from a naïve phage display library: Preliminary findings for antivenom development. Toxicon. 49: 699-709.

Viravan, C., Veeravat, U., Warrell, M. J., Theakston, R. D., Warrell, D. A. 1986. ELISA confirmation of acute and past envenoming by the monocellate Thai cobra (Naja kaouthia). Am. J. Trop. Med. Hyg. 35: 173-181.

Vu, K. B., Ghahroudi, M. A., Wyns, L., Muyldermans, S. 1997. Comparison of llama VH sequences from conventional and heavy chain antibodies. Mol. Immunol. 34: 1121-1131.

WHO. Rabies and envenomings. A neglected public health issue. Geneva: World Health Organization; 2007.

Yang, C. C. 1999. Cobrotoxin: structure and function. J Nat Toxins. 1999 June; 8(2):221-33)

What is claimed is:

1. A single-domain antibody (sdAb) that binds to snake venom metalloproteinase (SVMP), comprising an amino acid sequence which is at least 70% identical to SEQ ID NOs. 1 or 2.

2. A single-domain antibody (sdAb) that binds to snake venom metalloproteinase (SVMP), wherein the sdAb comprises at least one single-variable region that includes a plurality of complementarity-determining regions (CDRs) including:
   a CDR1 that exhibits 100% sequence identity to SEQ ID NOs. 6 or 7;
   a CDR2 that exhibits 100% sequence identity to SEQ ID NOs. 11 or 12; and
   a CDR3 that exhibits 100% sequence identity to SEQ ID NOs. 16 or 17.

3. The sdAb of claim 2, wherein the at least one single-variable region further includes a plurality of framework regions (FRs) and has a general formula:

FR1-CDR1-FR2-CDR2-FR3-CDR3-FR4, wherein:
   the FR1 exhibits 100% sequence identity to SEQ ID NOs. 21-22 or 26;
   the FR2 exhibits 100% sequence identity to SEQ ID NOs. 27-28 or 32;
   the FR3 exhibits 100% sequence identity to SEQ ID NOs. 33-34 or 38; and
   the FR4 exhibits 100% sequence identity to SEQ ID NOs. 39 or 41.

4. The sdAb of claim 2, wherein said sdAb is CDR-grafted, humanized, de-immunized, or selected by phage display.

5. A single-domain antibody (sdAb) that binds to snake bungarotoxin, comprising an amino acid sequence identical to SEQ ID NO. 3.

6. A single-domain antibody (sdAb) that binds to snake bungarotoxin, wherein the sdAb comprises at least one single-variable region that includes a plurality of complementarity-determining regions (CDRs) including:
   a CDR1 identical to SEQ ID NO. 8;
   a CDR2 identical to SEQ ID NO. 13; and
   a CDR3 identical to SEQ ID NO. 18.

7. The sdAb of claim 6, wherein the at least one single-variable region further includes a plurality of framework regions (FRs) and has a general formula:

FR1-CDR1-FR2-CDR2-FR3-CDR3-FR4, wherein
   the FR1 exhibits 100% sequence identity to SEQ ID NOs. 23 or 26;
   the FR2 exhibits 100% sequence identity to SEQ ID NOs. 29 or 32;
   the FR3 exhibits 100% sequence identity to SEQ ID NOs. 35 or 38; and
   the FR4 exhibits 100% sequence identity to SEQ ID NOs. 40 or 41.

8. The sdAb of claim 6, wherein said sdAb is CDR-grafted, humanized, de-immunized, or selected by phage display.

9. A single-domain antibody (sdAb) that binds to snake cobrotoxin, comprising an amino acid sequence identical to SEQ ID NO. 4.

10. A single-domain antibody (sdAb) that binds to snake cobrotoxin, wherein the sdAb comprises at least one single-variable region that includes a plurality of complementarity-determining regions (CDRs) including:
    a CDR1 identical to SEQ ID NO. 9;
    a CDR2 identical to SEQ ID NO. 14; and
    a CDR3 identical to SEQ ID NO. 19.

11. The sdAb of claim 10, wherein the at least one single-variable region further includes a plurality of framework regions (FRs) and has a general formula:

FR1-CDR1-FR2-CDR2-FR3-CDR3-FR4, wherein:
    the FR1 exhibits 100% sequence identity to SEQ ID NOs. 24 or 26;
    the FR2 exhibits 100% sequence identity to SEQ ID NOs. 30 or 32;
    the FR3 exhibits 100% sequence identity to SEQ ID NOs. 36 or 38; and
    the FR4 exhibits 100% sequence identity to SEQ ID NOs. 39 or 41.

12. The sdAb of claim 10, wherein said sdAb is CDR-grafted, humanized, de-immunized, or selected by phage display.

13. A single-domain antibody (sdAb) that binds to snake venom phospholipase A2 (svPLA2), comprising an amino acid sequence identical to SEQ ID NO. 5.

14. A single-domain antibody (sdAb) that binds to snake venom phospholipase A2 (svPLA2), wherein the sdAb comprises at least one single-variable region that includes a plurality of complementarity-determining regions (CDRs) including:
    a CDR1 identical to SEQ ID NO. 10;
    a CDR2 identical to SEQ ID NO. 15; and
    a CDR3 identical to SEQ ID NO. 20.

15. The sdAb of claim 14, wherein the at least one single-variable region further includes a plurality of framework regions (FRs) and has a general formula:

FR1-CDR1-FR2-CDR2-FR3-CDR3-FR4, wherein:
    the FR1 exhibits 100% sequence identity to SEQ ID NOs. 25 or 26;
    the FR2 exhibits 100% sequence identity to SEQ ID NOs. 31 or 32;
    the FR3 exhibits 100% sequence identity to SEQ ID NOs. 37 or 38; and the FR4 exhibits 100% sequence identity to SEQ ID NOs. 40 or 41.

16. The sdAb of claim 14, wherein said sdAb is CDR-grafted, humanized, de-immunized, or selected by phage display.

* * * * *